(12) United States Patent
Kang et al.

(10) Patent No.: US 8,853,164 B2
(45) Date of Patent: Oct. 7, 2014

(54) OLIGOPEPTIDE IMPROVING DIFFERENTIATION OF OSTEOBLASTS

(75) Inventors: Eun Jung Kang, Busan (KR); Tae Gwan Eom, Busan (KR); Gyu Ok Choi, Seoul (KR)

(73) Assignee: Osstemimplant Co., Ltd., Seoul (KR)

( * ) Notice: Subject to any disclaimer, the term of this patent is extended or adjusted under 35 U.S.C. 154(b) by 0 days.

(21) Appl. No.: 13/579,861

(22) PCT Filed: Feb. 26, 2010

(86) PCT No.: PCT/KR2010/001262
§ 371 (c)(1),
(2), (4) Date: Aug. 17, 2012

(87) PCT Pub. No.: WO2011/105648
PCT Pub. Date: Jan. 9, 2011

(65) Prior Publication Data
US 2012/0316118 A1    Dec. 13, 2012

(51) Int. Cl.
| | | |
|---|---|---|
| A61K 38/00 | (2006.01) | |
| A61K 38/04 | (2006.01) | |
| A61K 38/10 | (2006.01) | |
| C07K 4/00 | (2006.01) | |
| C07K 7/08 | (2006.01) | |
| A61L 27/54 | (2006.01) | |
| A61L 27/22 | (2006.01) | |
| A61L 27/56 | (2006.01) | |
| C07K 14/51 | (2006.01) | |

(52) U.S. Cl.
CPC ............ *C07K 14/51* (2013.01); *A61L 2300/252* (2013.01); *C07K 7/08* (2013.01); *A61L 2430/02* (2013.01); *A61L 2300/412* (2013.01); *A61L 27/54* (2013.01); *A61L 27/227* (2013.01); *A61L 27/56* (2013.01); *A61L 2430/12* (2013.01)
USPC ......... 514/16.7; 514/16.9; 514/21.4; 530/326

(58) Field of Classification Search
None
See application file for complete search history.

(56) References Cited

U.S. PATENT DOCUMENTS

| | | | | |
|---|---|---|---|---|
| 5,194,596 A | * | 3/1993 | Tischer et al. | 530/399 |
| 5,350,836 A | * | 9/1994 | Kopchick et al. | 530/399 |
| 7,323,542 B2 | | 1/2008 | Balian | |

FOREIGN PATENT DOCUMENTS

| | | |
|---|---|---|
| KR | 10-0879704 B1 | 1/2009 |
| WO | 2005/072403 A2 | 8/2005 |

OTHER PUBLICATIONS

Benjamin et al., 1998, Development 125:1591-1598.*
Vukicevic et al., 1996, PNAS USA 93:9021-9026.*
Shen et al., 2004, Eur. J. Neurosci. 20:2031-2037.*
Massague, 1987, Cell 49:437-8.*
Pilbeam et al., 1993, Bone 14:717-720.*

* cited by examiner

*Primary Examiner* — Elizabeth C Kemmerer
(74) *Attorney, Agent, or Firm* — Seed IP Law Group PLLC

(57) ABSTRACT

The present disclosure relates to oligopeptides applicable to a dental implant, which are selected from the group consisting of PEP7 (SEQ ID NO:1), PEP71 (SEQ ID NO:2), EP72 (SEQ ID NO:3), PEP73 (SEQ ID NO:4), PEP74 (SEQ ID NO:5), PEP75 (SEQ ID NO:6) and PEP76 (SEQ ID NO:7). The oligopeptides have very high reactivity for a BMP-specific receptor to increase osteoblastic differentiation and calcification, thereby showing improved osteointegration and osteogenesis.

13 Claims, 5 Drawing Sheets

OLIGOPEPTIDE IMPROVING DIFFERENTIATION OF OSTEOBLASTS

CROSS-REFERENCE TO RELATED APPLICATION

This application is a U.S. national stage application filed under 35 U.S.C. §371 of International Patent Application PCT/KR2010/001262, accorded an international filing date of Feb. 26, 2010; which application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 720152_403USPC_SEQUENCE_LISTING.txt. The text file is 2.5 KB, was created on Dec. 4, 2013, and is being submitted electronically via EFS-Web.

BACKGROUND

1. Technical Field

The present disclosure relates to oligopeptides having improved osteoblastic differentiation ability, and more particularly, to oligopeptides used for enhancing osteointegration and osteogenesis in dental implants.

2. Description of the Related Art

Optimal use of dental implants requires short induction periods of osteointegration. That is, if osteointegration is not successively achieved within a short period of time, the treatment period becomes longer and the success rate of an implant surgery is declined due to the fail of initial osteointegration. Accordingly, there is an absolute need to enhance osteointegration and osteogenesis abilities.

For this, it has been developed a method of directly coating a growth factor such as TGF-β (transforming growth factor-β), IGF-1 (Insulin-like growth factor-1) and the like or a physiologically active substance such as BMP (bone morphogenetic protein) for promoting the proliferation and differentiation of osteoblasts on the surface of an implant, or spreading the factor or substance around the detect site during implant procedures. However, the coating of the physiologically active substance on the surface of an implant before the implant surgery causes several problems in that such an active substance is required in a large amount and unable to effectively remain at the implanted site, and thus, its application range is very restrictive. Further, the coating of the active substance is conducted at extremely limited area, and thus, it is impossible to achieve effective osteanagenesis and osteointegration over the whole surface of an implant, and implant surgery costs increase. In addition, such an implant surgery is not yet standardized and is inefficient for the management of patient, thereby being difficult to be adopted as a standardized method of an implant surgery.

BMPs interact with BMP receptors (BMPRs) on the cell surface to initiate intracellular signal transduction and play an important role in formation of alveolar bone. BMP receptors belong to a TGF-β transmembrane serine-threonine kinase receptor family. Efficient intracellular signal transduction through ligand binding is achieved by the following the steps of: forming a heteromeric receptor complex between a type I receptor and a type II receptor, inducing cross-phosphorylation from the type II receptor to the type I receptor, activating the Smad signaling cascade, and then, expressing a target protein. The BMP receptor includes three kinds of the type I receptors (ActR-I, BMPR-IA, BMPR-IB) and three kinds of the type II receptors (ActR-II, ActR-IIB, BMPR-II). It has been reported that all BMPs of the TGF-β superfamily interact with BMPR-II which is bound to BMPR-IA or BMPR-IB, and ActR-II, ActR-IIB and ActR-I do not interact with BMP-4. These facts suggest that BMPR-IA or BMPR-IB and BMPR-II are BMP-specific receptors. Therefore, the development of oligonucleotide sequences having higher binding affinity to a BMP-specific receptor present on the cell surface can further efficiently induce osteoblastic differentiation.

Meanwhile, there are several patent documents in relation to the development of BMP-derived peptides for stimulating the differentiation and proliferation of osteoblasts and the introduction of the BMP-derived peptides into the surface of an implant.

Korean Patent Publication No. 2006-0110189 entitled "Synthetic peptides for treatment of dental implant surfaces" discloses oligopeptides represented by the formula R1-(A-B-C)n-R2-(A-B-C)m-L (wherein, R1 is H, an amino acid residue, a fatty acid residue or a biodegradable polymer main chain, R2 is a spacer, and L is a linker). Said oligopeptides can promote bone growth and shorten the induction period of osteointegration by being directly treated on the surface of a dental implant.

Korean Patent Publication No. 2006-0101019 (Patent No. 0676945) entitled "Bone graft and scaffolding materials immobilized with osteogenesis enhancing peptides on the surface" relates to bone graft and scaffolding materials whose surface is coated with a cell adhesion-inducing peptide and/or a tissue growth factor-derived peptide. In particular, it discloses osteogenesis protein (BMP-2, 4, 6)-derived peptides.

Korean Patent Publication No. 2006-0082060 (Patent No. 0630903) entitled "Membrane and implant immobilized osteogenic enhancing peptides on the surface" relates to a membrane and an implant in which a cell adhesion-inducing peptide or a tissue growth factor-derived peptide is coated on a crosslinker-bound surface. It discloses osteogenesis protein (BMP-2)-derived peptides.

However, the oligopeptides disclosed in said patent documents still fail dramatically to shorten the induction period of initial osteointegration.

Further, Korean Patent Application No. 2008-0054730 discloses oligopeptides having a specific sequence (as a key peptide, R1-CKIPKPSSAPTELSAISMLYL-R2 (SEQ ID NO: 8), referred to as 'PEP111') which shorten the induction period of initial osteointegration and promote osteogenesis (all of the patents referred to herein are hereby incorporated by reference in their entirety).

However, the oligopeptides disclosed in said patent application show very low binding affinity to a BMP-specific receptor, and thus, their osteointegration and osteogenesis abilities are not satisfactory. Accordingly, there is a need to develop oligopeptides having high binding affinity to a BMP-specific receptor (e.g., BMPR-IA and BMPR-II) to show excellent initial osteointegration and osteogenesis abilities.

BRIEF SUMMARY

The present disclosure provides oligopeptides having very high reactivity to BMP-specific receptors, BMPR-IA and BMPR-II, to improve binding affinity for the BMP-specific receptors of oligonucleotides disclosed in Korean Patent Application No. 2008-0054730.

The present disclosure also provides new oligopeptides capable of improving osteoblastic differentiation and calcification and increasing osteogenesis through the development of oligopeptides having very high reactivity to a BMP-specific receptor.

The present disclosure further provides a method of shortening the period of an implant surgery through the improvement of initial osteointegration by chemically introducing the oligopeptide disclosed herein into the surface of a dental implant.

DETAILED DESCRIPTION

Figure 1:
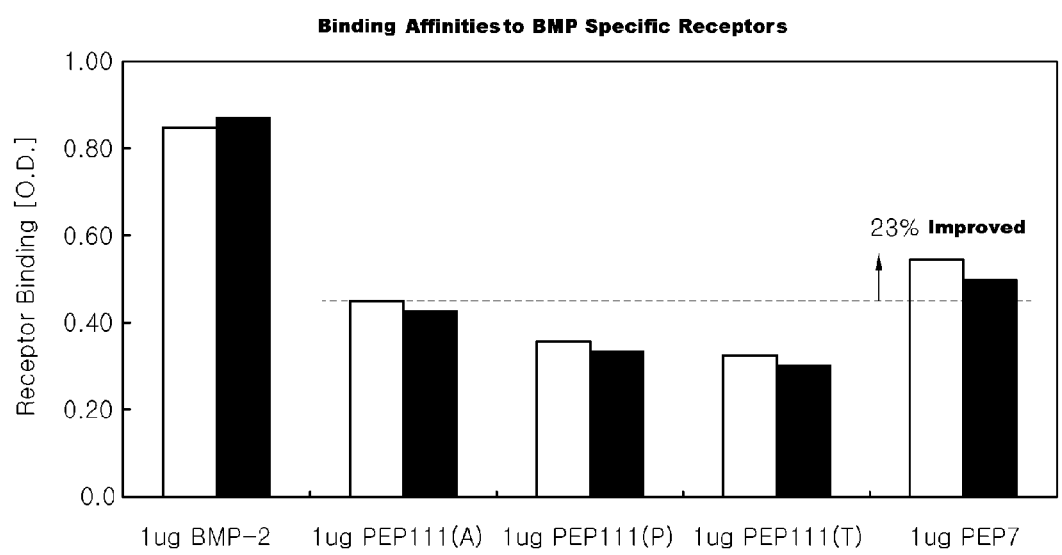
FIG. 1 is a graph showing binding affinities of oligopeptides to BMP-specific receptors (BMPR-1A (white bar) and BMP-II (black bar)).

Oligopeptides having certain amino acid sequences show significantly high reactivity to a BMP-specific receptor, thereby improving osteoblastic differentiation and calcification abilities.

The oligopeptides disclosed herein have considerably improved reactivities to a BMP-specific receptor by the replacement of an amino acid with another amino acid at a certain position of PEP 111 which is a representative oligopeptide disclosed in Korean Patent Application No. 2008-0054730.

The oligopeptides disclosed herein are characterized by having the amino acid sequence selected from the group consisting of amino acid sequences represented by SEQ ID NO:1 to 7, and can be used as an in vivo implant coating agent for shortening the induction period of osteointegration.

```
SEQ ID NO: 1:
PEP7            KIPKPSSVPTELSAISMLYL

SEQ ID NO: 2:
PEP71           IPKPSSVPTELSAISMLYL

SEQ ID NO: 3:
PEP72           PKPSSVPTELSAISMLYL

SEQ ID NO: 4:
PEP73           KPSSVPTELSAISMLYL

SEQ ID NO: 5:
PEP74           KIPKPSSVPTELSAISMLY

SEQ ID NO: 6:
PEP75           KIPKPSSVPTELSAISML

SEQ ID NO: 7:
PEP76           KIPKPSSVPTELSAISM
```

Further, the oligopeptides disclosed herein are applicable to implants, in particular to dental implants, and are preferably selected from the group consisting of PEP7 (SEQ ID NO:1), PEP71 (SEQ ID NO:2), PEP72 (SEQ ID NO:3), PEP73 (SEQ ID NO:4), PEP74 (SEQ ID NO:5), PEP75 (SEQ ID NO:) and PEP76 (SEQ ID NO:7), more preferably from the group consisting of PEP7, PEP71 and PEP74, still more preferably PEP7 or PEP71, and most preferably PEP7.

A matrix may preferably be introduced into the oligopeptides disclosed herein so as to control the distance between oligopeptides depending on the size of osteoblasts and regulate their relative orientation. In addition, the titanium surface of an implant can be pre-treated with a linker, and a —SH group-containing amino acid such as cysteine can be introduced into an N-terminal or a C-terminal end of the oligopeptides disclosed herein for the binding to a functional group of the linker.

For example, in connection with the linker, the oligopeptides disclosed herein contain cysteine at the N-terminal end to be easily introduced into the implant by means of the interaction between the linker and cysteine. Further, in order to stably introduce the oligopeptides disclosed herein into the titanium (Ti) surface of an implant, the oligopeptides may preferably be introduced into the implant surface in a linking relationship with a silane-linker-peptide.

In addition, it is possible to improve the stability of the oligopeptides disclosed herein through the acetylation of their N-terminal end and/or amidation of their C-terminal end.

The oligopeptides disclosed herein can be easily synthesized according to the conventional methods well-known to the person skilled in the art.

The oligopeptides disclosed herein show significantly improved reactivity to a BMP-specific receptor as compared to the prior art oligopeptide PEP111 to play an important role in the osteoblastic differentiation and proliferation, and considerably shorten the induction period of osteointegration on the application to the surface of an implant. In particular, it is predicted that the oligopeptides disclosed herein can be very useful to broaden the range of an implant surgery for patients with poor bone quality.

Further, in case of applying the oligopeptides disclosed herein to a barrier membrane and the surface of an implant, the oligopeptides may preferably be introduced at a concentration ranging from 0.1 to 5.0 mg per unit area. More preferably, the oligopeptides disclosed herein may have 10 to 21 amino acids content, and may be introduced into the surface of an implant at a concentration ranging from 0.1 to 3.0 mg per unit area.

The oligopeptides disclosed herein can be applied to the surface of an implant according to the conventional methods well-known in the art (e.g., the method disclosed in the relevant patent application described above) or the method disclosed herein. Here, it is possible to use a matrix or a linker. The above-identified patent application discloses a method of modifying the surface of an implant, a method of using a crosslinker, a method of using a matrix, a method of preparing a silane-linker-peptide, a method of coating an oligopeptide and the like.

Single-letter codes for each of the amino acids used as disclosed herein are letter codes currently used in the art, which are summarized in the following table.

| Single-letter code | Abbreviation | Full name |
|---|---|---|
| A | Ala | Alanine |
| R | Arg | Arginine |
| N | Asn | Asparagine |
| D | Asp | Aspartic acid |

| Single-letter code | Abbreviation | Full name |
|---|---|---|
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

The oligopeptides disclosed herein show very high reactivity to a BMP-specific receptor, thereby increasing their osteoblastic differentiation and calcification abilities, to obtain the efficient osteogenesis effect without the use of bone fillers. The implants using the oligopeptides disclosed herein can lead to the recruitment and activation of osteoblasts due to the continuous action of the oligopeptides treated on the surface of an implant in the form of a thin film, and thus, it can be expected to shorten the induction period of initial osteointegration, increase the probability of success for an implant surgery for patients with poor bone quality, induce osteogenesis without the use of bone fillers even in the case of low bone quantity, and reduce the cost for an implant surgery.

EXAMPLES

The following Examples provide particular embodiments. It should be understood that these Examples are given by way of illustration only. As a result, the present invention is not limited by the illustrative Examples set forth herein below, but rather is defined by the claims contained herein below. It will be apparent to those skilled in the art that many changes and modifications may be made without departing from the spirit and scope of the disclosure.

Example 1

Preparation of Oligopeptides

Oligopeptides were synthesized according to the Fmoc/tBu method, and subjected to HPLC after the synthesis was completed. As a result, the oligopeptides having a purity of 95% or more were purified, and their molecular weight was examined by NMR.

Specifically, thus selected oligopeptide sequences are as follows.

```
SEQ ID NO: 1:
PEP7            KIPKPSSVPTELSAISMLYL

SEQ ID NO: 2:
PEP71           IPKPSSVPTELSAISMLYL

SEQ ID NO: 3:
PEP72           PKPSSVPTELSAISMLYL

SEQ ID NO: 4:
PEP73           KPSSVPTELSAISMLYL

SEQ ID NO: 5:
PEP74           KIPKPSSVPTELSAISMLY

SEQ ID NO: 6:
PEP75           KIPKPSSVPTELSAISML

SEQ ID NO: 7:
PEP76           KIPKPSSVPTELSAISM
```

Among these oligopeptides, PEP7 of SEQ ID NO:1 was subjected to the following experiments.

Text Example 1

BMP Specific Binding Assay

PEP7 (1 µg/well) was added to an ELISA plate and incubated at 4° C. for 12 hours. After PEP7 was coated on the plate, BMPR-IA or BMPR-II (1 µg/well) was added thereto and reacted at room temperature for 2 hours, to obtain a PEP7-BMP receptor complex. A primary antibody specific for a BMP receptor (0.5 µg BMR-IA, BMPR-II) was added to the complex and reacted at room temperature for 1 hour. A secondary antibody (BMPR-IA or BMPR-II-Fc Ab-HRP) was then added to the resulting mixture and reacted at room temperature for 1 hour. After ABTS was added to the resulting mixture and reacted at room temperature for 30 minutes, an absorbance of the resulting mixture was measure at 595 nm (FIG. 1, wherein PEP111(A) means the sequence whose $9^{th}$ amino acid was alanine, PEP111(P) means the sequence whose alanine was replaced with proline, and PEP111(T) means the sequence whose alanine was replaced with threonine). As a result, it has been found that the oligopeptide disclosed herein shows a binding affinity of about 23% higher to a BMP-specific receptor than PEP111. These results have confirmed that the PEP7 oligopeptide exhibits far superior binding affinity to a BMP-specific receptor, as compared to PEP111.

Test Example 2

Initial Cell Differentiation Ability Assay

Figure 2:
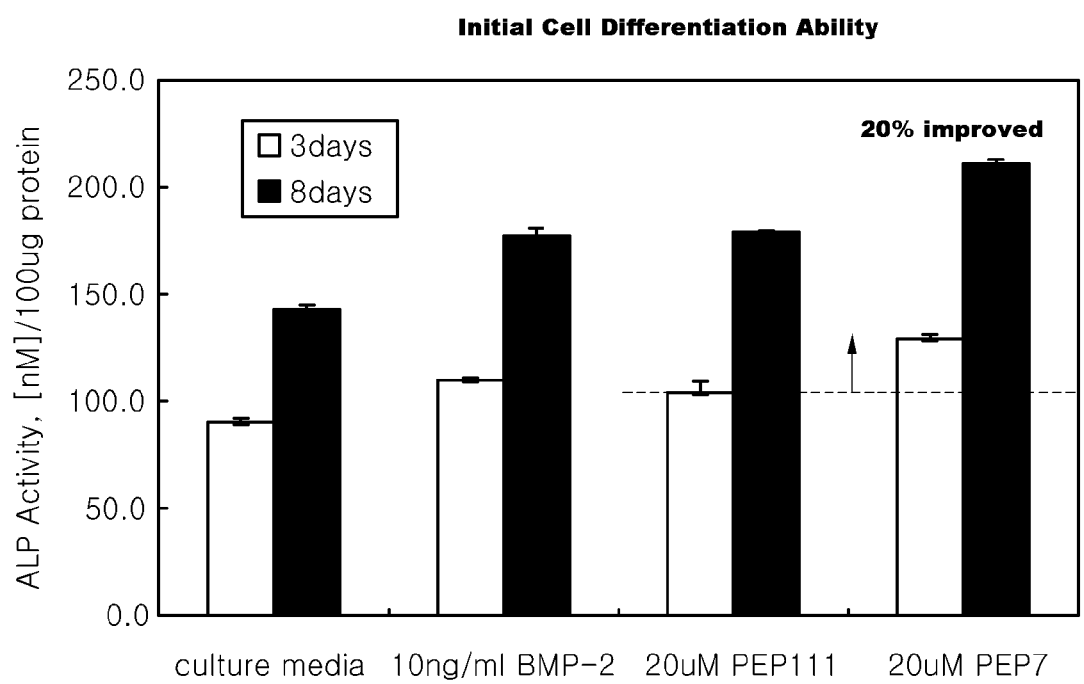
FIG. 2 is a graph showing alkaline phosphatase activities of oligopeptides as an initial cell differentiation ability marker of osteoblasts.

The effect of the oligopeptide disclosed herein on osteoblastic differentiation was examined by comparing ALP (alkaline phosphatase) activity as an initial differentiation marker of osteoblasts. In order to compare the differentiation ability of osteoblasts, MG63 cells were distributed to a 24-well plate at a concentration of $1 \times 10^5$ cells and incubated for 1 day. Then, the cell was treated with each of the PEP7 oligopeptide disclosed herein, and positive controls BMP-2 and PEP111 in a differentiation culture medium and incubated in a 37° C. $CO_2$ incubator. The medium was replaced with a fresh one at 2-day intervals, the ALP activity was measured at Day 3 and 8 after the cultivation (FIG. 2). It has been found that the PEP7 oligopeptide shows an ALP activity of 20% higher than PEP111, which suggests the considerable improvement in differentiation ability of osteoblasts.

Test Examples 3, 4

Late Cell Differentiation Ability Assay

Figure 3:
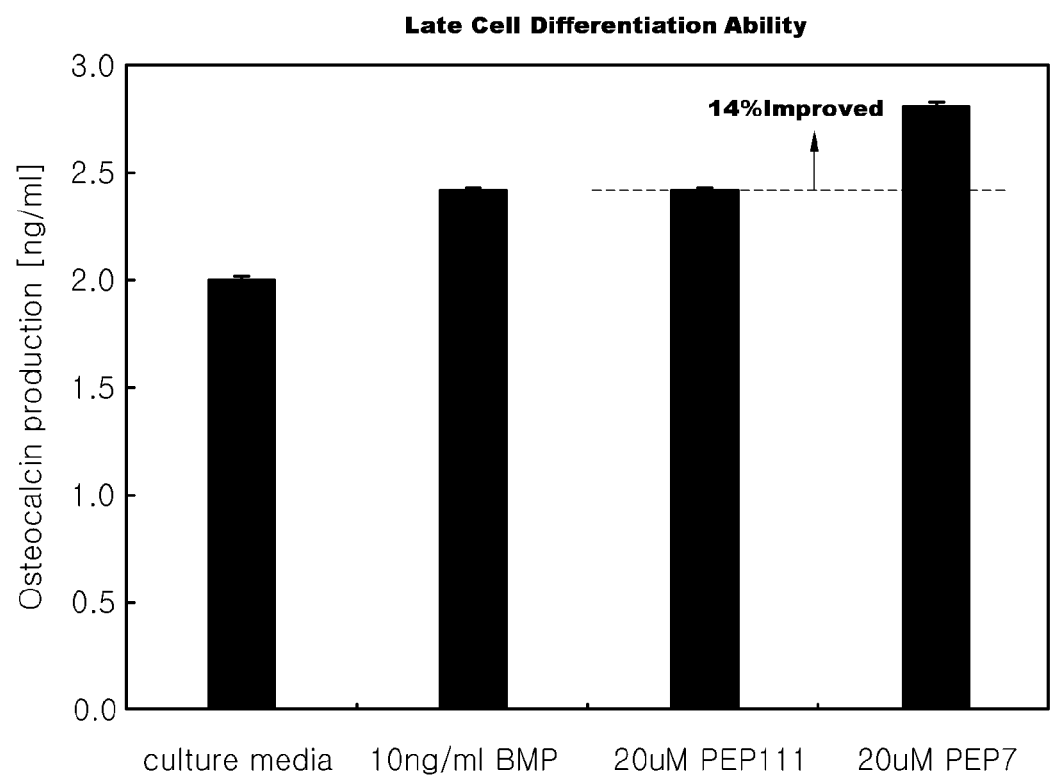
FIG. 3 is a graph showing osteocalcin production abilities of oligopeptides as a late cell differentiation ability marker of osteoblasts.
Figure 4:
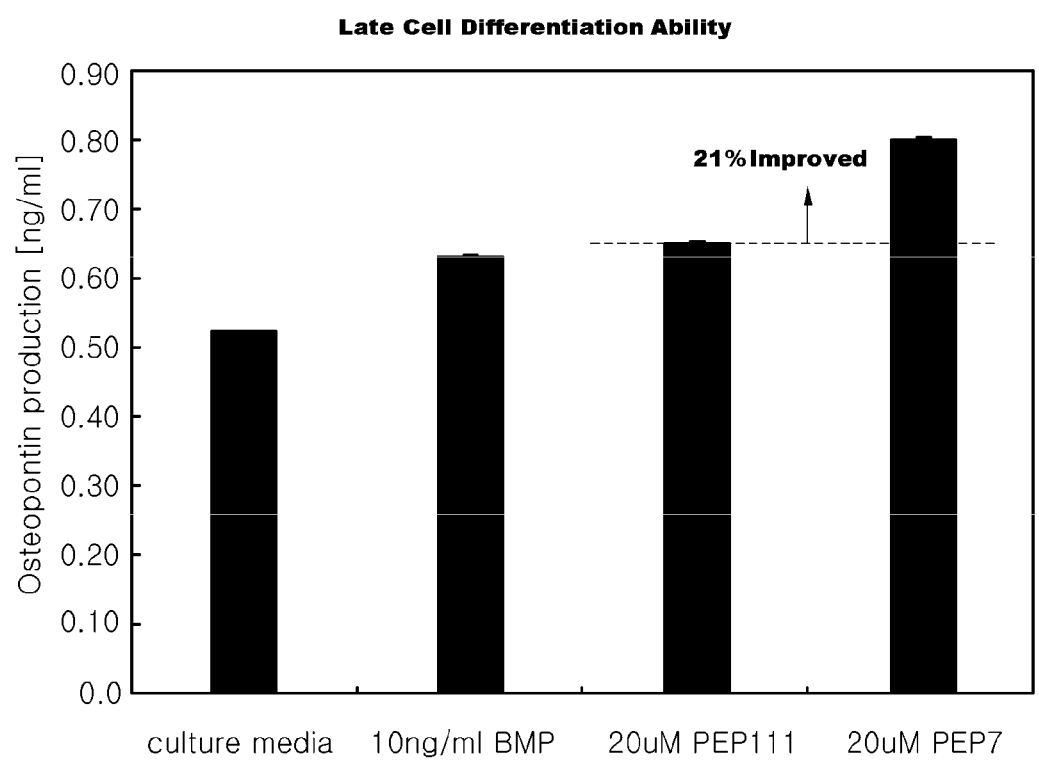
FIG. 4 is a graph showing osteopontin production abilities of oligopeptides as a late cell differentiation ability marker of osteoblasts.

The effect of the PEP7 oligopeptide on osteoblastic differentiation was examined by comparing the production amount of osteocalcin and osteopontin as a late differentiation marker of osteoblasts. The cultivation was carried out according to the same conditions as described above. At Day 14, the culture solution was harvested, and the amount of osteocalcin and osteopontin therein was measured by using a human ELISA kit (FIGS. 3 and 4). It has been found that the PEP7 oligopeptide produces an osteocalcin degree of about 14% or more and an osteopontin degree of about 21% or more than PEP 111, which suggests that the oligopeptide of the present invention can significantly increases late cell differentiation ability.

Test Example 5

Calcification Ability Assay

Figure 5:
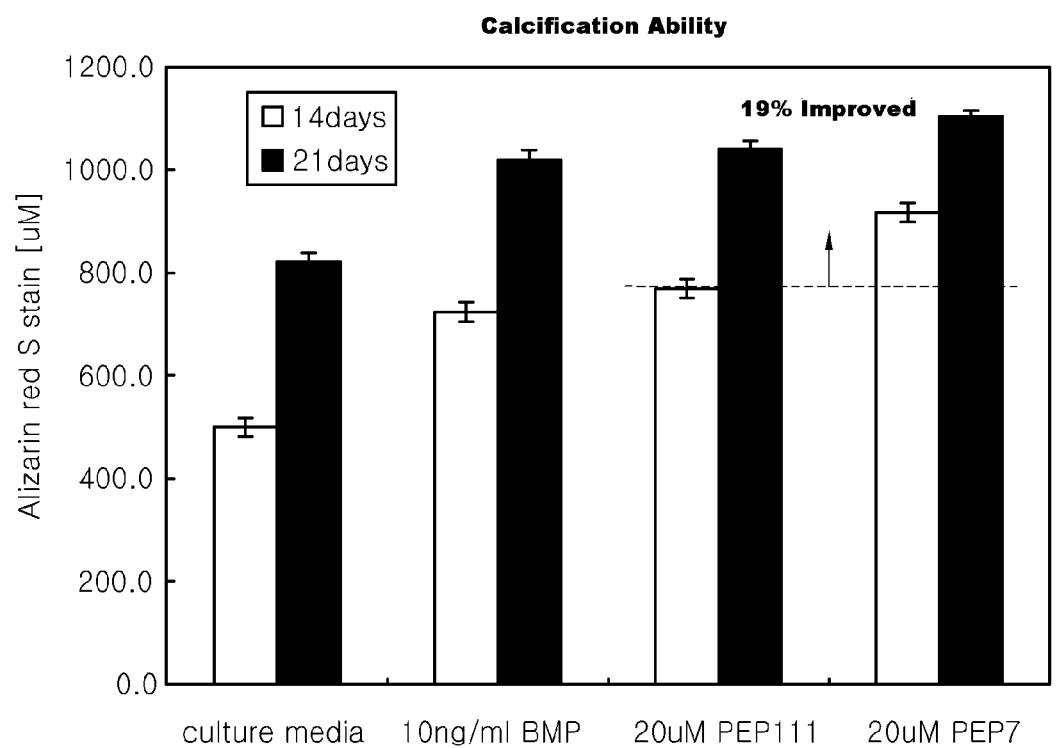
FIG. 5 is a graph showing extracellular matrix calcification abilities resulting from osteogenic differentiation induced by the inventive oligopeptides.

In order to examine whether the oligopeptide disclosed herein can successfully induce osteogenic differentiation, extracellular matrix calcification was observed. The cultivation was carried out according to the same conditions as described above. At Day 14 and 21, the culture solution was harvested and subjected to Alizarin red S staining (FIG. 5). As a result, it has been found that at Day 14, the PEP7 oligopeptide shows a calcification ability of about 19% higher than PEP111, which suggests that the oligopeptide disclosed herein can improve osteogenic differentiation.

As previously described, the oligopeptides disclosed herein show very high reactivity to a BMP-specific receptor as compared to the prior art oligopeptide PEP111, thereby increasing their osteoblastic differentiation and calcification abilities. Therefore, the oligopeptides disclosed herein can improve the replacement effect of bone fillers and osteogenesis effect.

The oligopeptides disclosed herein have excellent binding affinity to a BMP-specific receptor to promote osteoblastic differentiation. Thus, the oligopeptides disclosed herein are coated on the surface of an implant in the form of a thin film, thereby shortening the induction period of initial osteointegration, increasing the success probability of an implant surgery for patients with poor bone quality, and inducing osteogenesis without the use of bone fillers even in the case of low bone quantity.

The invention claimed is:

1. An oligopeptide for in vivo use, comprising any one of the amino acid sequences set forth in SEQ ID NO:1 to SEQ ID NO:7.

2. The oligopeptide of claim 1, wherein the oligopeptide is comprises the amino acid sequence SEQ ID NO:1.

3. The oligopeptide of claim 1, wherein a cysteine is added to the N-terminal or the C-terminal end of the oligopeptide.

4. The oligopeptide of claim 1 or 2, wherein the N-terminal end of the oligopeptide is acetylated.

5. The oligopeptide of claim 1 or 2, wherein the C-terminal end of the oligopeptide is amidated.

6. The oligopeptide of claim 1 or 2, wherein the N-terminal end of the oligopeptide is acetylated and the C-terminal end of the oligopeptide is amidated.

7. An oligopeptide agent for in vivo use, comprising one or more oligopeptides of claim 1.

8. A method for improving osteogenesis and osteointegration after implant surgery, comprising introducing into a surface of a dental implant one or more oligopeptides of claim 1, thereby improving osteogenesis and osteointegration after implant surgery.

9. The method according to claim 8, wherein the oligopeptide comprises SEQ ID NO:1.

10. The method according to claim 8, wherein a cysteine is added to the N-terminal or the C-terminal end of the oligopeptide.

11. The method according to claim 8 or 9, wherein the N-terminal end of the oligopeptide is acetylated.

12. The method according to claim 8 or 9, wherein the C-terminal end of the oligopeptide is amidated.

13. The method according to claim 8 or 9, wherein the N-terminal end of the oligopeptide is acetylated and the C-terminal end of the oligopeptide is amidated.

* * * * *

UNITED STATES PATENT AND TRADEMARK OFFICE
CERTIFICATE OF CORRECTION

PATENT NO. : 8,853,164 B2
APPLICATION NO. : 13/579861
DATED : October 7, 2014
INVENTOR(S) : Eun Jung Kang et al.

It is certified that error appears in the above-identified patent and that said Letters Patent is hereby corrected as shown below:

Title Page

Item (87):
"Jan. 9, 2011" should read, --Sep. 1, 2011--.

Item (57):
"The present disclosure relates to oligopeptides applicable to a dental implant, which are selected from the group consisting of PEP7 (SEQ ID NO:1), PEP71 (SEQ ID NO:2), EP72 (SEQ ID NO:3), PEP73 (SEQ ID NO:4), PEP74 (SEQ ID NO:5), PEP75 (SEQ ID NO:6) and PEP76 (SEQ ID NO:7). The oligopeptides have very high reactivity for a BMP-specific receptor to increase osteoblastic differentiation and calcification, thereby showing improved osteointegration and osteogenesis." should read, --The present disclosure relates to oligopeptides applicable to a dental implant, which are selected from the group consisting of PEP7 (SEQ ID NO:1), PEP71 (SEQ ID NO:2), PEP72 (SEQ ID NO:3), PEP73 (SEQ ID NO:4), PEP74 (SEQ ID NO:5), PEP75 (SEQ ID NO:6) and PEP76 (SEQ ID NO:7). The oligopeptides have very high reactivity for a BMP-specific receptor to increase osteoblastic differentiation and calcification, thereby showing improved osteointegration and osteogenesis.--.

Claims

Column 11, Lines 5-6:
"2. The oligopeptide of claim 1, wherein the oligopeptide is comprises the amino acid sequence SEQ ID NO:1." should read, --2. The oligopeptide of claim 1, wherein the oligopeptide comprises the amino acid sequence SEQ ID NO:1--.

Signed and Sealed this
Twenty-seventh Day of October, 2015

Michelle K. Lee
*Director of the United States Patent and Trademark Office*

```
                          SEQUENCE LISTING

<160> NUMBER OF SEQ ID NOS: 8

<210> SEQ ID NO 1
<211> LENGTH: 20
<212> TYPE: PRT
<213> ORGANISM: Artificial Sequence
<220> FEATURE:
<223> OTHER INFORMATION: PEP7

<400> SEQUENCE: 1

Lys Ile Pro Lys Pro Ser Ser Val Pro Thr Glu Leu Ser Ala Ile Ser
1               5                   10                  15

Met Leu Tyr Leu
            20

<210> SEQ ID NO 2
<211> LENGTH: 19
<212> TYPE: PRT
<213> ORGANISM: Artificial Sequence
<220> FEATURE:
<223> OTHER INFORMATION: PEP71

<400> SEQUENCE: 2

Ile Pro Lys Pro Ser Ser Val Pro Thr Glu Leu Ser Ala Ile Ser Met
1               5                   10                  15

Leu Tyr Leu

<210> SEQ ID NO 3
<211> LENGTH: 18
<212> TYPE: PRT
<213> ORGANISM: Artificial Sequence
<220> FEATURE:
<223> OTHER INFORMATION: PEP72

<400> SEQUENCE: 3

Pro Lys Pro Ser Ser Val Pro Thr Glu Leu Ser Ala Ile Ser Met Leu
1               5                   10                  15

Tyr Leu

<210> SEQ ID NO 4
<211> LENGTH: 17
<212> TYPE: PRT
<213> ORGANISM: Artificial Sequence
```

```
<220> FEATURE:
<223> OTHER INFORMATION: PEP73

<400> SEQUENCE: 4

Lys Pro Ser Ser Val Pro Thr Glu Leu Ser Ala Ile Ser Met Leu Tyr
1               5                   10                  15

Leu

<210> SEQ ID NO 5
<211> LENGTH: 19
<212> TYPE: PRT
<213> ORGANISM: Artificial Sequence
<220> FEATURE:
<223> OTHER INFORMATION: PEP74

<400> SEQUENCE: 5

Lys Ile Pro Lys Pro Ser Ser Val Pro Thr Glu Leu Ser Ala Ile Ser
1               5                   10                  15

Met Leu Tyr

<210> SEQ ID NO 6
<211> LENGTH: 18
<212> TYPE: PRT
<213> ORGANISM: Artificial Sequence
<220> FEATURE:
<223> OTHER INFORMATION: PEP75

<400> SEQUENCE: 6

Lys Ile Pro Lys Pro Ser Ser Val Pro Thr Glu Leu Ser Ala Ile Ser
1               5                   10                  15

Met Leu

<210> SEQ ID NO 7
<211> LENGTH: 17
<212> TYPE: PRT
<213> ORGANISM: Artificial Sequence
<220> FEATURE:
<223> OTHER INFORMATION: PEP76

<400> SEQUENCE: 7

Lys Ile Pro Lys Pro Ser Ser Val Pro Thr Glu Leu Ser Ala Ile Ser
1               5                   10                  15

Met

<210> SEQ ID NO 8
<211> LENGTH: 21
<212> TYPE: PRT
<213> ORGANISM: Artificial Sequence
<220> FEATURE:
<223> OTHER INFORMATION: Synthetic oligopeptide that shortens the
      induction period of initial osteointegration and promotes
      osteogenesis

<400> SEQUENCE: 8

Cys Lys Ile Pro Lys Pro Ser Ser Ala Pro Thr Glu Leu Ser Ala Ile
1               5                   10                  15

Ser Met Leu Tyr Leu
            20
```